United States Patent
Artzberger

(10) Patent No.: US 7,020,903 B2
(45) Date of Patent: Apr. 4, 2006

(54) COMBINATION EYE AND EAR PROTECTION APPARATUS

(76) Inventor: Bill Artzberger, P.O. Box 33032, Bloomfield Hills, MI (US) 48303

( * ) Notice: Subject to any disclaimer, the term of this patent is extended or adjusted under 35 U.S.C. 154(b) by 126 days.

(21) Appl. No.: 10/767,033

(22) Filed: Jan. 29, 2004

(65) Prior Publication Data
US 2004/0181841 A1    Sep. 23, 2004

Related U.S. Application Data

(60) Provisional application No. 60/443,468, filed on Jan. 30, 2003.

(51) Int. Cl.
*A61F 9/02* (2006.01)

(52) U.S. Cl. .............................. 2/431; 2/6.3; 2/6.7; 2/15
(58) Field of Classification Search .................... 2/6.3, 2/6.7, 15
See application file for complete search history.

(56) References Cited

U.S. PATENT DOCUMENTS

| 4,682,374 A | | 7/1987 | Geiser |
| 4,856,089 A | | 8/1989 | Horton |
| 4,945,573 A | | 8/1990 | Landis |
| 5,133,596 A | * | 7/1992 | Korny et al. ............... 351/158 |
| 5,278,999 A | * | 1/1994 | Brown et al. .................. 2/209 |
| 6,481,846 B1 | * | 11/2002 | Mikysa ........................ 351/158 |

* cited by examiner

*Primary Examiner*—Katherine Moran
*Assistant Examiner*—Alissa J. Tompkins

(57) ABSTRACT

A combination eye and ear protection apparatus includes an eye protection portion which includes respective ends, an ear protection portion which includes a pair of ear-covering portions, and a pair of bridge portions connected between the respective ends of the eye protection portion and outer portions of the respective ear-covering portions. The eye protection portion includes a frame which includes frame ends, and lenses are received in the frame. The bridge portions include VELCRO bridge-to-ear-cover connectors and the ear-covering portions include complimentary VELCRO ear-cover-to-bridge connectors. With the combination eye and ear protection apparatus of the invention both ear protection and eye protection are provided for a wearer without the eye protection assembly interfering with good ear protection.

10 Claims, 3 Drawing Sheets

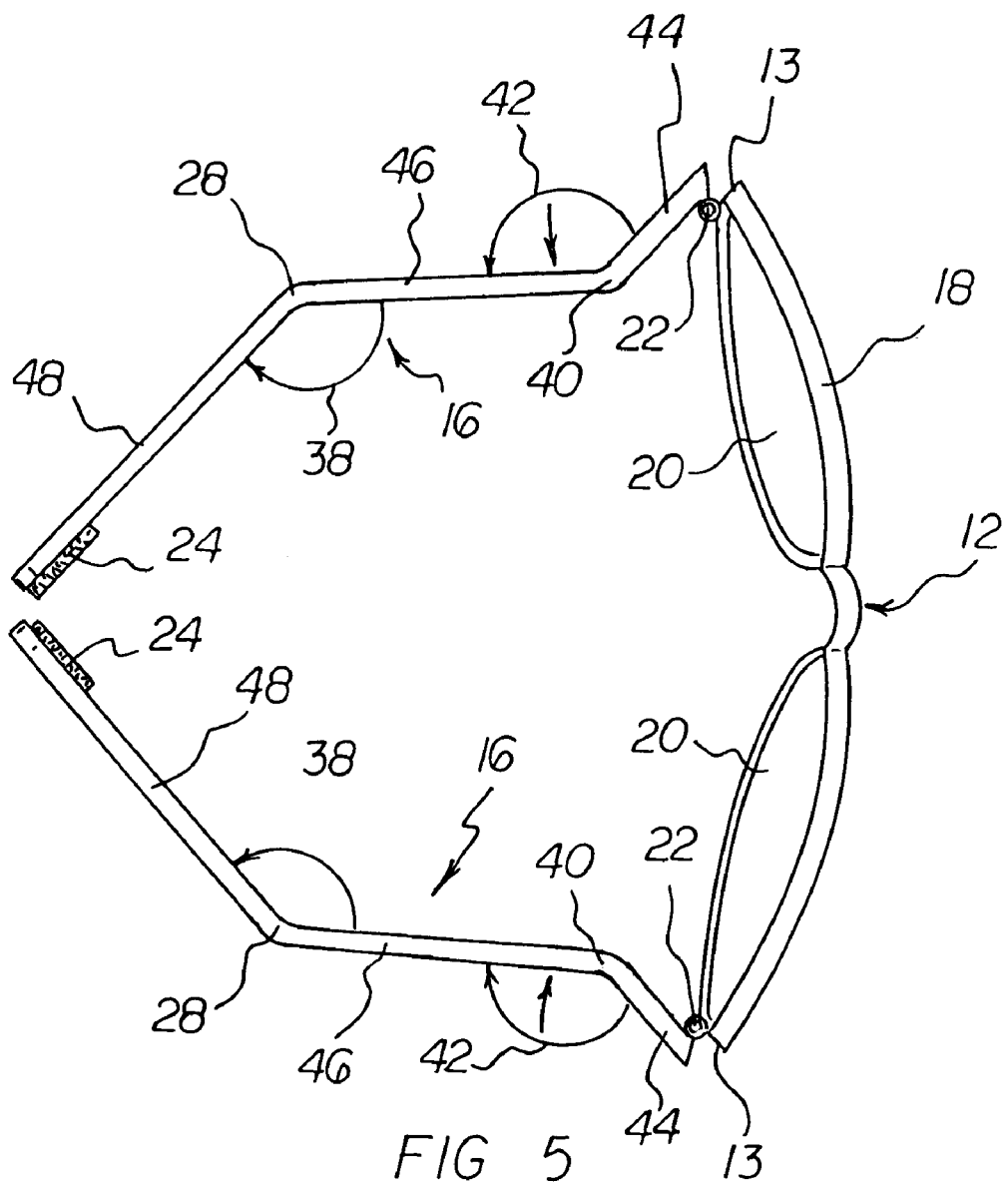

COMBINATION EYE AND EAR PROTECTION APPARATUS

CROSS-REFERENCE TO RELATED APPLICATION

This application claims priority based upon my now abandoned Provisional Application Ser. No. 60/443,468, filed Jan. 30, 2003.

BACKGROUND OF THE INVENTION

1. Field of the Invention

The present invention relates generally to protective devices worn by a user and, more particularly, to devices especially adapted for protective the user's eyes and ears.

2. Description of the Prior Art

Devices worn by a user to protect the users eyes and ears are well known in the art. The eyes may need protection from air borne particles, and the ears may need protection from excessive noise. In this respect, throughout the years, a number of innovations have been developed relating to user-worn eye and ear protective devices, and the following U.S. patents are representative of some of those innovations: U.S. Pat. Nos. 4,682,374, 4,856,089, 5,133,596, and 5,278,999.

More specifically, U.S. Pat. No. 4,682,374 discloses a user-worn eye and ear protective device which discloses substantially straight connecting members between the eye protecting portions and the ear protecting portions. Because of the differences in dimensions between a person's eyes and a person's ears, it would be desirable if a user-worn eye and ear protective device which includes connecting members between the eye protecting portions and the ear protecting portions which had bends to accommodate the differences in distance between the user's eyes and the user's ears.

U.S. Pat. No. 4,856,089 discloses a user-worn eye and ear protective device in which the eye protection portions are connected to the ear protection portions by means of an overhead connection. The eye protection portions and the ear protection portions are not connected together with connecting members which extend along the sides of a user's head. Significant stability is achieved when eye protection portions and ear protection portions are connected together with connecting members which extend along the sides of a user's head. In this respect, it would be desirable if a user-worn eye and ear protective device were provided which includes connecting members which extend along the sides of a user's head.

U.S. Pat. No. 5,133,596 discloses a user-worn eye and ear protective device which has connecting members which extend along the sides of a user's head. More specifically, the ear protection portions are connected to the connecting members to the eye protection portions using a rider member and a slot in which the rider member rides. In this respect, the ear protection portions and the connecting members are essentially permanently attached to each other. If the ear protection portions need to be cleaned or replaced, it is a relatively difficult and time-consuming task to separate the ear protection portions from the connecting members. In view of the above, it would be desirable if a user-worn eye and ear protective device were provided in which the ear protection portions can easily be removed from and attached to the connecting members to the eye protection portions.

U.S. Pat. No. 5,278,999 discloses a user-worn eye and ear protective device in which the connecting members between the eye protection portions and the ear protection portions are connected to the ear protection portions by means of hinge pins. As described above with respect to U.S. Pat. No. 5,133,596, it is a relatively difficult and time-consuming task to separate the ear protection portions from the connecting members when hinge pins are used to connected the ear protection portions and the connecting members to the eye protection portions.

U.S. Pat. No. 4,945,573 may also be of interest for its disclosure of a user-worn eye protective device.

Thus, while the foregoing body of prior art indicates it to be well known to use a combination eye and ear protection apparatus, the prior art described above does not teach or suggest a combination eye and ear protection apparatus which has the following combination of desirable features: (1) includes connecting members between the eye protecting portions and the ear protecting portions which have bends to accommodate the differences in distance between the user's eyes and the user's ears; (2) includes connecting members which extend along the sides of a user's head; and (3) provides ear protection portions which can easily be removed from and attached to the connecting members to the eye protection portions. The foregoing desired characteristics are provided by the unique combination eye and ear protection apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a combination eye and ear protection apparatus which includes an eye protection portion which includes respective ends, an ear protection portion which includes a pair of ear-covering portions, and a pair of bridge portions connected between the respective ends of the eye protection portion and the respective ear-covering portions. The eye protection portion includes a frame which includes frame ends, and lenses are received in the frame. With the combination eye and ear protection apparatus of the invention both ear protection and eye protection are provided for a wearer without the eye protection assembly interfering with good ear protection.

Preferably, a pair of bridge-to-frame hinges are connected between the pair of bridge portions and the frame ends. Also, preferably, a pair of bridge-to-ear-cover connectors are connected to distal ends of the bridge portions, and a pair of ear-cover-to-bridge connectors are connected to outer portions of the ear-covering portions.

Preferably, each of the bridge portions includes a first bridge segment connected to a bridge-to-frame hinge. A second bridge segment is connected to the first bridge segment at a first bend which has an outer bend angle, and a third bridge segment is connected to the second bridge segment at a second bend which has an inner bend angle. Preferably, the inner bend angle is substantially equal to the outer bend angle. Preferably, the inner bend angle and the outer bend angle are obtuse angles. The inner bend angle and the outer bend angle provide an offset distance between the frame ends and ends of the bridge portions. The inner bend angle and the outer bend angle are approximately 120 degrees.

Preferably, the bridge-to-ear-cover connectors are comprised of first hook-or-loop connectors, and the ear-cover-to-bridge connectors are comprised of second hook-or-loop connectors. Preferably, the ear protection portion is in a form of a headset.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved combination eye and ear protection apparatus which has all of the advantages of the prior art and none of the disadvantages.

It is another object of the present invention to provide a new and improved combination eye and ear protection apparatus which may be easily and efficiently manufactured and marketed.

It is a further object of the present invention to provide a new and improved combination eye and ear protection apparatus which is of durable and reliable construction.

An even further object of the present invention is to provide a new and improved combination eye and ear protection apparatus which is susceptible of a low cost of manufacture with regard to both materials and labor, and which accordingly is then susceptible of low prices of sale to the consuming public, thereby making such combination eye and ear protection apparatus available to the buying public.

Still yet a further object of the present invention is to provide a new and improved combination eye and ear protection apparatus which includes connecting members between the eye protecting portions and the ear protecting portions which have bends to accommodate the differences in distance between the user's eyes and the user's ears.

Still another object of the present invention is to provide a new and improved combination eye and ear protection apparatus that includes connecting members which extend along the sides of a user's head.

Yet another object of the present invention is to provide a new and improved combination eye and ear protection apparatus which provides ear protection portions which can easily be removed from and attached to the connecting members to the eye protection portions.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 4 is an enlarged partial inside view of a portion of the embodiment of the invention shown in FIG. 3 taken along line 4—4 thereof.

FIG. 5 is a top view of the embodiment of the invention shown in FIG. 3, wherein the temple portions are rotated inwardly around their respective hinges.

DESCRIPTION OF THE PREFERRED EMBODIMENT

Figure 1:
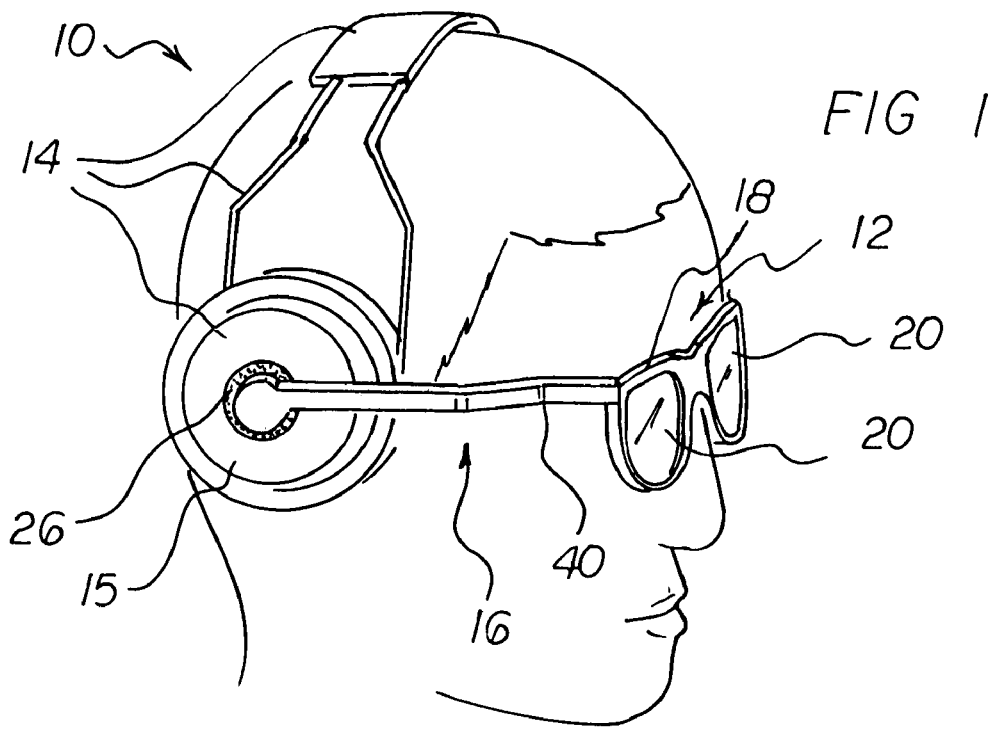
FIG. 1 is a top perspective view showing a preferred embodiment of the combination eye and ear protection apparatus of the invention being worn by a person.
Figure 2:
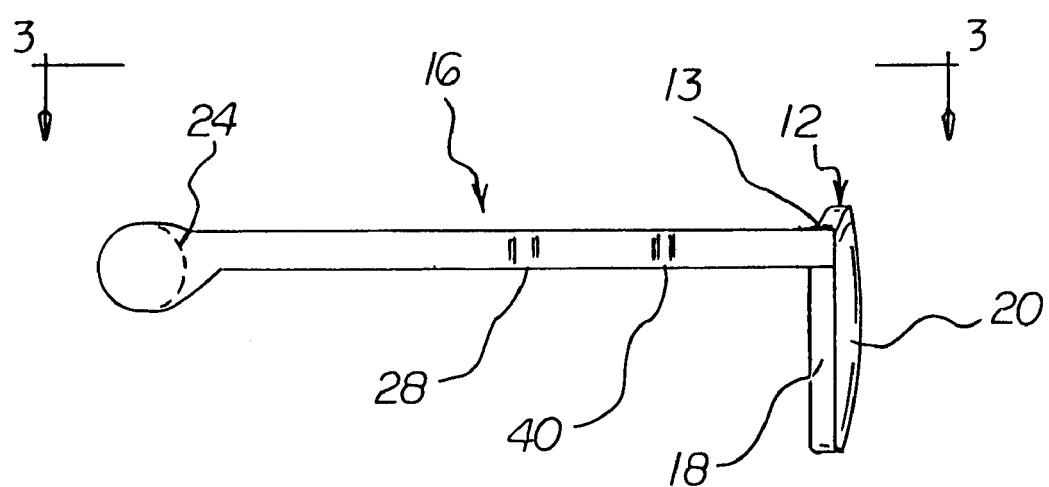
FIG. 2 is an enlarged side view of the embodiment of the combination eye and ear protection apparatus shown in FIG. 1, removed from the person.
Figure 3:
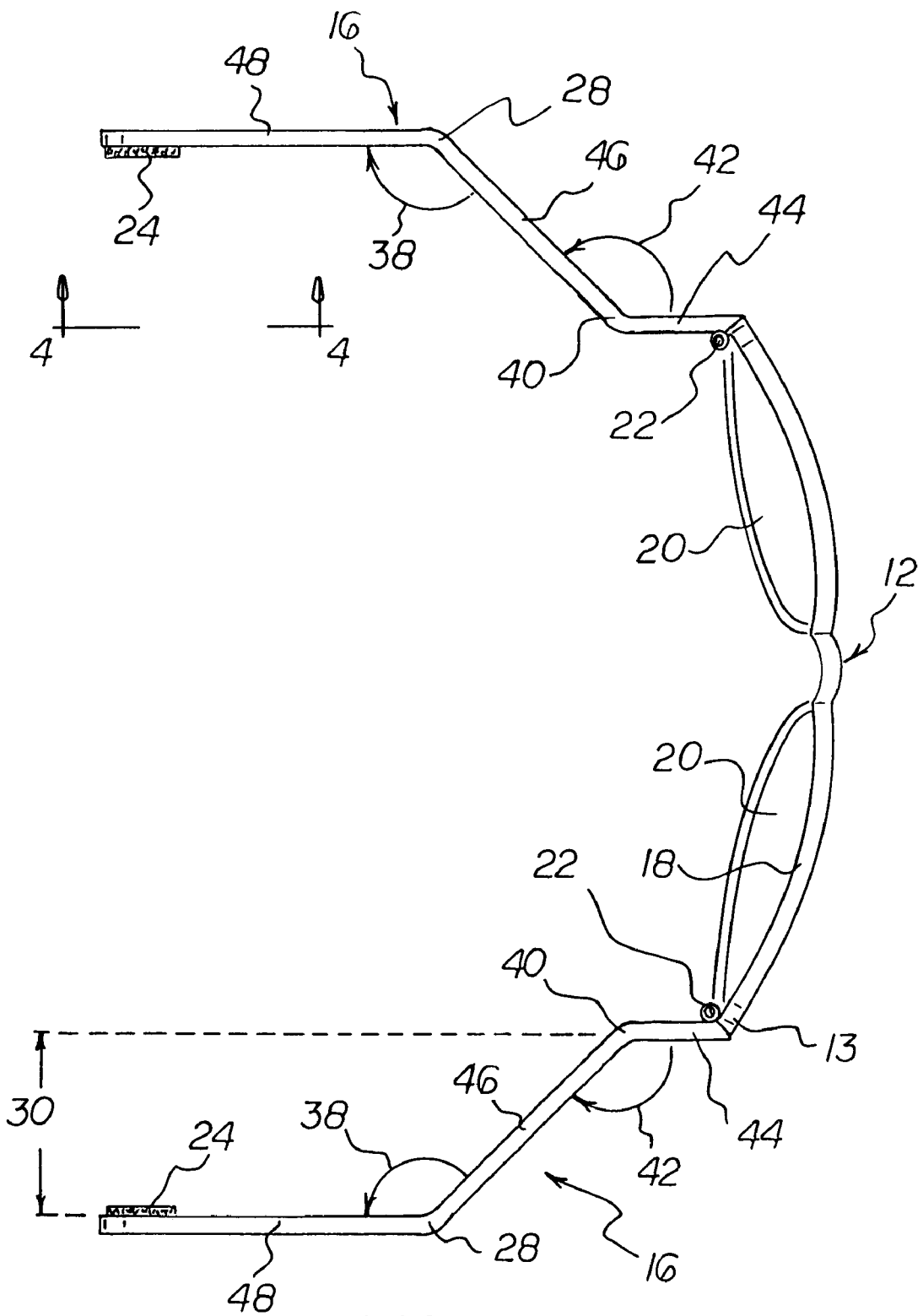
FIG. 3 is a top view of the embodiment of the combination eye and ear protection apparatus of FIG. 2 taken along line 3—3 thereof.

With reference to the drawings, a new and improved combination eye and ear protection apparatus embodying the principles and concepts of the present invention will be described.

Turning to FIGS. 1–5, there is shown a preferred embodiment of the combination eye and ear protection apparatus of the invention generally designated by reference numeral 10. In the preferred embodiment, the combination eye and ear protection apparatus 10 an eye protection portion 12 which includes respective ends 13, an ear protection portion 14 which includes a pair of ear-covering portions 15, and a pair of bridge portions 16 connected between the respective ends 13 of the eye protection portion 12 and the respective ear-covering portions 15. The eye protection portion 12 includes a frame 18 which includes frame ends 13, and lenses 20 are received in the frame 18.

Preferably, a pair of bridge-to-frame hinges 22 are connected between the pair of bridge portions 16 and the frame ends 13. Also, preferably, a pair of bridge-to-ear-cover connectors 24 are connected to distal ends of the bridge portions 16, and a pair of ear-cover-to-bridge connectors 26 are connected to outer portions of the ear-covering portions 15.

Preferably, each of the bridge portions 16 includes a first bridge segment 44 connected to a bridge-to-frame hinge 22. A second bridge segment 46 is connected to the first bridge segment 44 at a first bend 40 which has an outer bend angle 42, and a third bridge segment 48 is connected to the second bridge segment 46 at a second bend 28 which has an inner bend angle 38. Preferably, the inner bend angle 38 is substantially equal to the outer bend angle 42. Preferably, the inner bend angle 38 and the outer bend angle 42 are obtuse angles. The inner bend angle 38 and the outer bend angle 42 provide an offset distance 30 between the frame ends 13 and ends of the bridge portions 16. The inner bend angle 38 and the outer bend angle 42 are approximately 120 degrees.

Preferably, the bridge-to-ear-cover connectors 24 are comprised of first hook-or-loop connectors, and the ear-cover-to-bridge connectors 26 are comprised of second hook-or-loop connectors. The first hook-or-loop connectors and the second hook-or-loop connectors can be made from VELCRO(™) material. Preferably, the ear protection portion 14 is in a form of a headset 14.

To use the combination eye and ear protection apparatus 10 of the invention, a headset 14 in accordance with the invention is placed on a person's 20 head, as shown in FIG. 1. The eye protection portion 12 and the bridge portions 16 are formed as an integrated, unified structure, like a pair of conventional eyeglasses, forming an integrated eye protection/bridges assembly. Then, the integrated eye protection/bridges assembly is placed on a person, like a conventional pair of eyeglasses, as shown in FIG. 1, and the VELCRO bridge-to-ear-cover connectors 24 are attached to the VELCRO ear-cover-to-bridge connectors 26. When this is done, the headset 14 and the integrated eye protection/bridges assembly are secured together, thereby providing protection for the wearer's eyes and ears. Moreover, the secure connection between the integrated eye protection/bridges assembly and the headset 14 prevents the combination eye and ear protection apparatus 10 of the invention from falling off of the wearer's head.

The respective first bend 40, outer bend angle 42, second bend 28, and inner bend angle 38 provide the offset distance 30 so that the VELCRO bridge-to-ear-cover connectors 24 at the ends of the third bridge segments 48 are positioned at the outer surfaces of the ear-covering portions 15 where the VELCRO ear-cover-to-bridge connectors 26 are located. As a result, because the bridge portions 16 are not under the ear-covering portions 15 between the ear-covering portions 15 and the wearer's head, the seals between the ear-covering portions 15 and the wearer's head are not broken by the bridge portions 16.

When the eye protection portion 12 is to be removed from the headset 14, 20 the VELCRO bridge-to-ear-cover connectors 24 are easily separated from the VELCRO ear-cover-to-bridge connectors 26 so that the integrated eye protection/bridges assembly can easily be removed from the wearer. When this is done, the headset 14 can be left on the wearer's head, if desired to continue with ear protection, without eye protection.

The components of the combination eye and ear protection apparatus of the invention can be made from inexpensive and durable metal, plastic, and glass materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved combination eye and ear protection apparatus that is low in cost, relatively simple in design and operation, and which may advantageously include connecting members between the eye protecting portions and the ear protecting portions which have bends to accommodate the differences in distance between the user's eyes and the user's ears. With the invention, a combination eye and ear protection apparatus is provided which includes connecting members which extend along the sides of a user's head. With the invention, a combination eye and ear protection apparatus provides ear protection portions which can easily be removed from and attached to the connecting members to the eye protection portions.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

The invention claimed is:

1. A combination eye and ear protection apparatus, comprising:
   an eye protection portion which includes respective ends,
   an ear protection portion which includes a pair of ear-covering portions,
   a pair of bridge portions connected between said respective ends of said eye protection portion and said respective ear-covering portions,
   a pair of bridge-to-frame hinges connected between said pair of bridge portions and frame ends,
   a pair of bridge-to-ear-cover connectors connected to distal ends of said bridge portions, and
   a pair of ear-cover-to-bridge connectors connected to outer portions of said ear-covering portions,
   wherein said bridge-to-ear-cover connectors are comprised of first hook-or-loop connectors, and said ear-cover-to-bridge connectors are comprised of second hook-or-loop connectors,
   wherein each of said bridge portions includes:
   a first bridge segment connected to a bridge-to-frame hinge,
   a second bridge segment connected to said first bridge segment at a first bend which has an outer bend angle, and
   a third bridge segment connected to said second bridge segment at a second bend which has an inner bend angle, and
   wherein said inner bend angle is substantially equal to said outer bend angle.

2. The apparatus of claim 1 wherein said ear protection portion is in a form of a headset.

3. The apparatus of claim 1 wherein said eye protection portion includes:
   a frame which includes frame ends, and
   lenses received in said frame.

4. A combination eye and ear protection apparatus, comprising:
   an eye protection portion which includes respective ends,
   an ear protection portion which includes a pair of ear-covering portions, a pair of bridge portions connected between said respective ends of said eye protection portion and said respective ear-covering portions,
a pair of bridge-to-frame hinges connected between said pair of bridge portions and frame ends,
a pair of bridge-to-ear-cover connectors connected to distal ends of said bridge portions, and
a pair of ear-cover-to-bridge connectors connected to outer portions of said ear-covering portions.
wherein said bridge-to-ear-cover connectors are comprised of first hook-or-loop connectors, and said ear-cover-to-bridge connectors are comprised of second hook-or-loop connectors,
wherein each of said bridge portions includes:
a first bridge segment connected to a bridge-to-frame hinge,
a second bridge segment connected to said first bridge segment at a first bend which has an outer bend angle, and
a third bridge segment connected to said second bridge segment at a second bend which has an inner bend angle, and
wherein said inner bend angle and said outer bend angle are obtuse angles.

5. The apparatus of claim 4 wherein said inner bend angle and said outer bend angle are approximately 120 degrees.

6. The apparatus of claim 4 wherein said ear protection portion is in a form of a headset.

7. The apparatus of claim 4 wherein said eye protection portion includes:
a frame which includes frame ends, and
lenses received in said frame.

8. A combination eye and ear protection apparatus, comprising:
an eye protection portion which includes respective ends,
an ear protection portion which includes a pair of ear-covering portions,
a pair of bridge portions connected between said respective ends of said eye protection portion and said respective ear-covering portions,
a pair of bridge-to-frame hinges connected between said pair of bridge portions and frame ends,
a pair of bridge-to-ear-cover connectors connected to distal ends of said bridge portions, and
a pair of ear-cover-to-bridge connectors connected to outer portions of said ear-covering portions,
wherein said bridge-to-ear-cover connectors are comprised of first hook-or-loop connectors, and said ear-cover-to-bridge connectors are comprised of second hook-or-loop connectors,
wherein each of said bridge portions includes:
a first bridge segment connected to a bridge-to-frame hinge,
a second bridge segment connected to said first bridge segment at a first bend which has an outer bend angle, and
a third bridge segment connected to said second bridge segment at a second bend which has an inner bend angle, and
wherein said inner bend angle and said outer bend angle provide an offset distance between said frame ends and ends of said bridge portions.

9. The apparatus of claim 8 wherein said ear protection portion is in a form of a headset.

10. The apparatus of claim 8 wherein said eye protection portion includes:
lenses received in said frame.

* * * * *